US009572978B2

United States Patent
Bernhard et al.

(10) Patent No.: US 9,572,978 B2
(45) Date of Patent: Feb. 21, 2017

(54) ELECTRO STIMULATION TREATMENT APPARATUS AND METHOD

(75) Inventors: Axel L. Bernhard, Sydney (AU); Alan Cook, Hallett Cove (AU)

(73) Assignee: SKOP GmbH Ltd, Tortola (VG)

( * ) Notice: Subject to any disclaimer, the term of this patent is extended or adjusted under 35 U.S.C. 154(b) by 0 days.

(21) Appl. No.: 13/565,849

(22) Filed: Aug. 3, 2012

(65) Prior Publication Data

US 2013/0066388 A1    Mar. 14, 2013

Related U.S. Application Data

(63) Continuation of application No. 10/734,925, filed on Dec. 12, 2003, now abandoned.

(30) Foreign Application Priority Data

Dec. 12, 2002    (AU) ................................ 2002953278

(51) Int. Cl.
*A61N 1/08* (2006.01)
*A61N 1/36* (2006.01)
*A61N 1/32* (2006.01)

(52) U.S. Cl.
CPC ............... *A61N 1/08* (2013.01); *A61N 1/326* (2013.01); *A61N 1/36014* (2013.01)

(58) Field of Classification Search
CPC ...... A61N 1/08; A61N 1/326; A61N 1/36014; A61N 1/323; A61N 1/328

(Continued)

(56) References Cited

U.S. PATENT DOCUMENTS 3,279,468 A * 10/1966 Le Vine ................. 607/140
3,610,250 A * 10/1971 Sarbacher ............... 607/149

(Continued)

FOREIGN PATENT DOCUMENTS

JP    11-099190    4/1999
JP    11-169381    6/1999

(Continued)

OTHER PUBLICATIONS

Koji et al.; English machine translation of JP 11-169381 published Jun. 29, 1999; 16 pages.

(Continued)

*Primary Examiner* — George Evanisko
(74) *Attorney, Agent, or Firm* — Moore & Van Allen PLLC; Peter B. Stewart

(57) ABSTRACT

An electro stimulation system for providing signals to a subject including:
at least one electrical power supply;
a first switching device for intermittently connecting the output of an electrical power supply to one or more connection probes electrically connected to the subject;
a second switching device for intermittently connecting one or more connection probes electrically connected to the subject to form an electrical current return path for current supplied by the electrical power supply; and
switching control devices connected to the first and second switching devices; wherein the intermittent connection of the output of an electrical power supply or the intermittent formation of electrical current return paths vary during a treatment and wherein the switching of the first and second devices occurs independently of each other.

9 Claims, 9 Drawing Sheets

(58) Field of Classification Search
USPC ............................. 607/66, 46, 67, 70, 140
See application file for complete search history.

(56) References Cited

U.S. PATENT DOCUMENTS

| | | | | |
|---|---|---|---|---|
| 4,390,023 | A | * | 6/1983 | Rise ................. 607/66 |
| 4,632,117 | A | * | 12/1986 | James ............... 607/46 |
| 4,969,468 | A | | 11/1990 | Byers et al. |
| 4,996,987 | A | | 3/1991 | Petrofsky |
| 5,052,391 | A | * | 10/1991 | Silberstone et al. ........... 607/46 |
| 5,063,929 | A | | 11/1991 | Bartelt et al. |
| 5,514,165 | A | | 5/1996 | Malaugh et al. |
| 5,527,357 | A | * | 6/1996 | Springer, Jr. ................ 607/140 |
| 5,895,416 | A | | 4/1999 | Barreras, Sr. et al. |
| 5,922,012 | A | * | 7/1999 | Sakano ........................ 607/46 |
| 6,516,227 | B1 | | 2/2003 | Meadows et al. |
| 6,597,947 | B1 | | 7/2003 | Inoue et al. |
| 6,631,296 | B1 | | 10/2003 | Parramon et al. |
| 6,944,503 | B2 | * | 9/2005 | Crowe et al. .................. 607/66 |
| 2002/0103513 | A1 | * | 8/2002 | Minogue ............... A61N 1/321 607/46 |

FOREIGN PATENT DOCUMENTS

| | | |
|---|---|---|
| JP | 2000-237331 | 9/2000 |
| WO | WO97/31679 | 9/1997 |
| WO | WO00/53113 | 9/2000 |
| WO | WO02/36002 | 5/2002 |

OTHER PUBLICATIONS

Shin et al.; English machine translation of JP 11-099190 published Apr. 13, 1999; 24 pages.

Iwao et al.; English machine translation of JP 2000-237331 published Sep. 5, 2000; 9 pages.

* cited by examiner

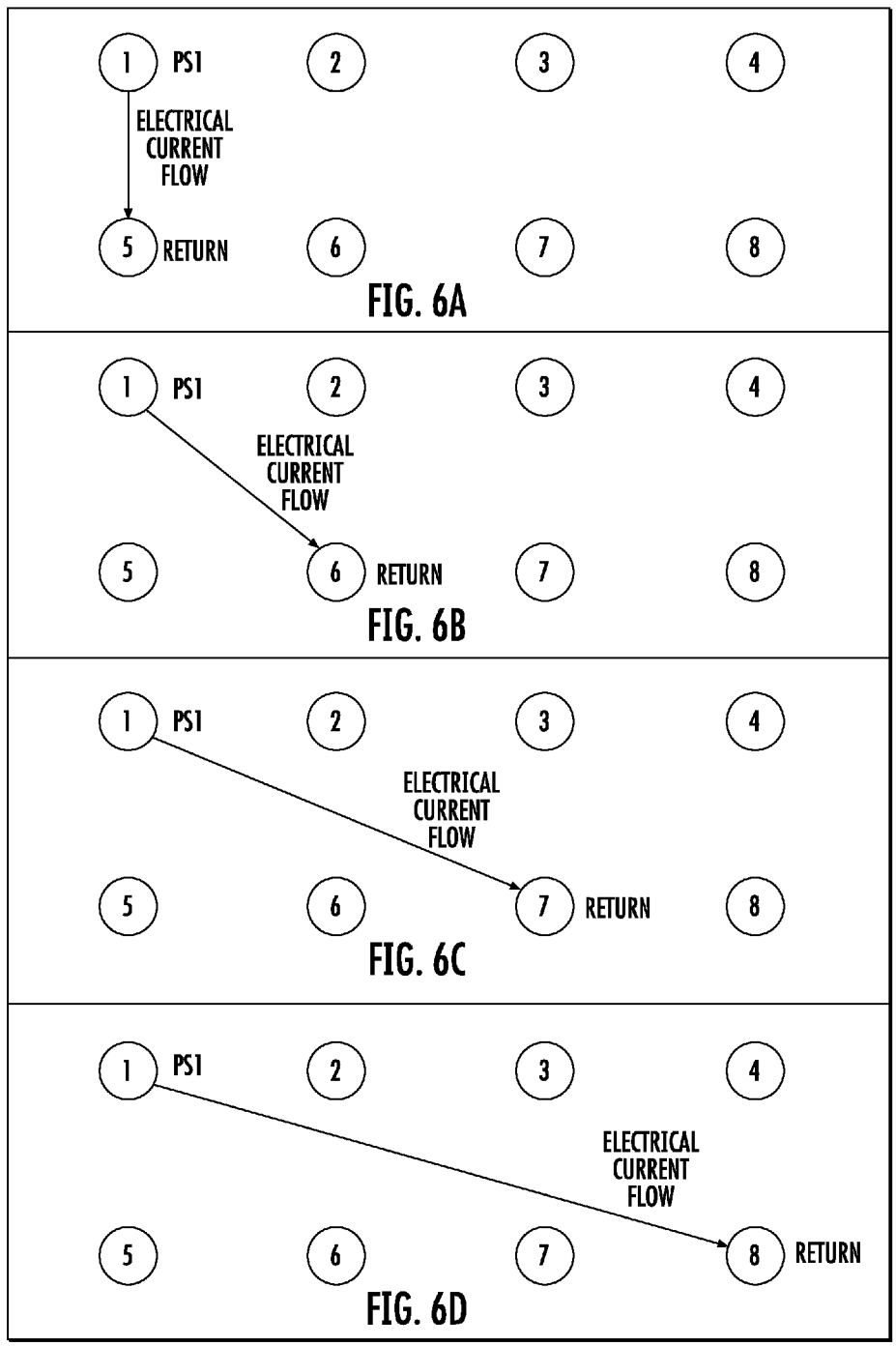

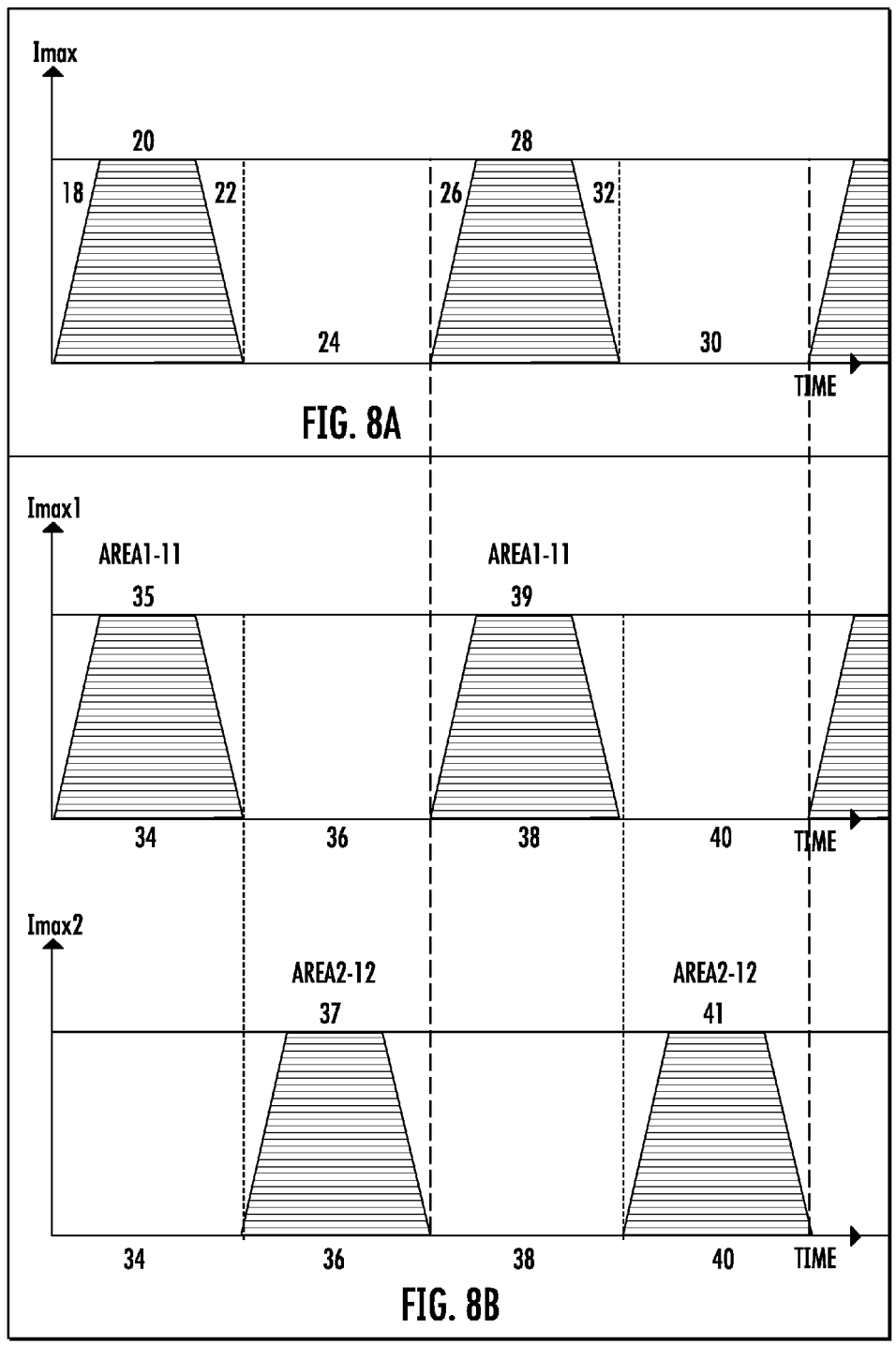

ELECTRO STIMULATION TREATMENT APPARATUS AND METHOD

CROSS-REFERENCE TO RELATED APPLICATIONS

This application claims priority to U.S. patent application Ser. No. 10/734,925, filed Dec. 12, 2003, entitled "Electro Stimulation Treatment Apparatus and Method," the entirety of which is incorporated herein by reference.

FIELD OF THE INVENTION

The invention relates generally to a method and apparatus for electro stimulation treatment of the body, cells or tissue cultures wherein electrical power is applied to a plurality of probes that are in electrical connection with the subject of the treatment. The invention is particularly suited to the treatment of any areas or areas of the body with electrical currents for cosmetic and/or medical purposes that currently require a relatively high level of manual intervention and operation by a skilled operator.

BACKGROUND OF THE INVENTION

Electro stimulation apparatus that provides micro current treatments gained popularity in the mid 1980's. The advent of electro stimulation treatment apparatus provided medical and cosmetic benefits although they required a relatively high level of intervention by operators providing long periods of "hands on" treatments. Similarly, clients/patients (herein referred to as subject) were required to spend relatively lengthy periods of time at clinics in order to receive treatments.

Since the advent of electro stimulation treatment apparatus, it has been generally recognized that there is a need to reduce the requirement for manual operation of the apparatus by a skilled operator. Apart from the requirement to locate sufficiently skilled operators, clinics have recognized that the labor cost of operators represents a significant component of the cost of delivery of these types of treatments. Further, over time, it has been noticed that clients are becoming less willing to spend the time required to attend clinics to receive treatments.

In addition to the problems identified above, there is a further problem in ensuring the efficacy of any treatment provided to a subject.

According to current treatment regimes, the efficacy of any treatment is highly dependent upon the skill and experience of an operator. Treatments are presently applied by the placement of probes on the surface of the skin of a subject and whilst signals are applied to the probes they are moved across the surface of the skin. Even with a highly skilled and experienced operator, it is currently impossible to ensure that an area being treated is uniformly exposed to electro stimulation.

Non-uniform exposure of an area requiring treatment will usually result in reduced efficacy of the treatment. In these instances, a subject may require more treatments than necessary to achieve the result they require and hence will necessarily be required to devote more time to receiving treatments than would otherwise be required.

Accordingly, there is a need for an electro stimulation treatment apparatus that reduces the requirement for manual operation by a skilled operator. Further, there is a need for such an apparatus that can provide a greater level of confidence that uniform treatment, or at least prescribed treatment, has been applied for any particular treatment session thereby reducing the amount time required to ensure effective treatment has been provided.

In the past, attempts have been made to provide a treatment apparatus that generates electrical signals and distributes those electrical signals to multiple probes that are in contact with the skin tissue of a subject. Generally, multiple "active" probes are provided that are electrically connected to a power supply and another set of multiple probes are also supplied that provide a return path for electrical current flow. Placement of "active" probes and "return" probes spaced apart on the body of a subject then allows the application of electrical signals to the active probes to cause a flow of electrical current through the area of the body residing between the active and return probes.

While this approach provides for a greater area to be treated, in past systems, substantially the same electrical signal is applied to all of the active probes at the same time. As a result, there is no assurance with respect to uniformity of application of the electrical currents to the area being treated as certain regions within that area may present a lower impedance path to the flow of electrical current and hence cause a concentration of the treatment through that region to the exclusion or limitation of other regions within the area being treated.

Other attempts to overcome the problems of non-uniform treatment have included systems having numerous power supplies that are connected to sub sets of probes such that placement of a set of active probes on the skin tissue of a subject comprises probes that are connected to different power supplies. Switching the individual power supplies on and off intermittently thus enables some control of the application of the electro stimulation treatment to the area being treated. However, these systems are intended to be used for the application of electro stimulation to disparate parts of the body, such as the legs and arms, so that these separate areas can be treated simultaneously. If all of the probes are located in a single area then substantial interference is caused between the power supplies.

Accordingly, it is an object of the present invention to provide an apparatus and method for the application of electro stimulation treatments to a treatment subject that provides greater uniformity of treatment as compared with prior art systems. It is a further object of the present invention to provide improved uniformity and efficiency of treatment as compared with prior art systems whilst retaining either a single power supply or a limited number of power supplies in the treatment apparatus thus maintaining the cost of such an apparatus to a minimum.

Any discussion of documents, devices, acts or knowledge in this specification is included to explain the context of the invention. It should not be taken as an admission that any of the material formed part of the prior art base or the common general knowledge in the relevant art on or before the date of filing of this application.

SUMMARY OF THE INVENTION

In one aspect, the present invention provides an electro stimulation system for providing signals to a subject including: at least one electrical power supply; a first switching device for intermittently connecting the output of an electrical power supply to one or more connection probes electrically connected to the subject; a second switching device for intermittently connecting one or more connection probes electrically connected to the subject to form an electrical current return path for current supplied by the electrical power supply; and switching control devices connected to the first and second switching devices; wherein the intermittent connection of the output of an electrical power supply or the intermittent formation of electrical current return paths vary during a treatment and wherein the switching of the first and second devices occurs independently of each other.

Preferably, the output of an electrical power supply is connected to a current control circuit such that electrical current supplied to the subject is regulated or controlled. Preferably, the switching device is a multiplexing device connected to a multiplexing control device.

As will be recognized by those skilled in the art, the first and second switching devices may be realized as separate units or may both reside within a single unit or apparatus such as an integrated circuit. Further, the first and second switching devices may be separate from the one or more electrical power supplies or may reside within a single housing along with the one or more supplies.

In the instance of using an apparatus according to a preferred embodiment for electro stimulation of skin tissue, electrical power is supplied through "active" connecting probes and electrical current return paths are established through "return" connecting probes connected to the skin tissue of a subject such that the supply of electrical signals to the skin of the subject through the multiplexing device causes electrical current to flow between one or more "active" probes and one or more "return" probes.

In an embodiment, the arrangement of "active" probes and "return" probes primarily determines the path of electrical current flow through an area to be treated. In a particularly preferred embodiment of the apparatus, the determination of the probes as either "active" or "return" type probes is determined by the multiplexing control device. In this embodiment, each probe is connected to a first multiplexing device with the connection to the probe configured as an output of the device. Simultaneously, each probe is also connected to a second multiplexing device with the connection to the probe configures as an input to the device. The first multiplexing device connects one or more probes to the output of the current control circuitry whilst the second multiplexing device connects one or more probes to an electrical current return path. Of course, during a treatment, a probe should only be either an active or return type probe at any one time. Connection of the outputs of the multiplexing devices allows any particular probe to be switched many times between the two types (i.e. active or return) during a treatment but any individual probe should not be selected as an active probe (i.e. connected to the output of the current control circuitry through the first multiplexer) at the same time that it is selected as a return probe (i.e. connected to the return path through the second multiplexer).

The connection arrangement of probes and the ability to control the type of the probe at any particular time during a treatment enables the provision of complex electrical current distributions amongst a set of probes connected to an area for treatment.

In another aspect, the present invention provides a controlled electrical signal supply for supplying electrical currents to a subject, said electrical current flowing through an area of the subject by connection of same with at least one active and return probe wherein, an electrical power supply is connected to the at least one active probe; a first electrical resistance is connected in parallel with the active and return probe; and the junction between the probe and the first resistance is connected to a ground reference through a controllable variable conductance network.

The first electrical resistance is preferably chosen to be significantly greater than the expected resistance presented between active and return probes in the area of the subject. In the instance of providing a treatment to a subject, the connection of a first resistance in parallel with the active and return probes substantially reduces the incidence of a stinging sensation when active probes are first attached to a treatment area. The choice of a significantly greater resistance as compared with the inter probe resistance of a treatment area also ensures that the majority of electrical current from a power supply passes through the area being treated.

The junction between the return probe and the first resistance is connected to a ground reference through a controlled variable conductance network. In this respect, controlling the conductance of the network substantially controls the amount of electrical current flowing through the area under treatment.

In a particularly preferred embodiment, the variable conductance network includes a conductance path formed by a collector-emitter path through a transistor in series connection with a second electrical resistance. With this particular arrangement, the voltage at the junction of the emitter and the second resistance varies proportionally with the electrical current flowing through the area under treatment. This junction may then be connected to a control signal network to enable the generation of a control signal for the base input of the transistor.

Preferably, the control signal network includes an operational amplifier receiving one input from the conductance network connected to the junction of the emitter and the second resistance and a second input from a digital to analogue converter (DAC). The operational amplifier is preferably configured as a differential amplifier with the input from the DAC connected to the non-inverting input and the output from the conductance network, providing a voltage proportional to the electrical current flowing through the area under treatment, connected to the inverting input.

In the preferred arrangement, the voltage signal output from the DAC represents the electrical current that will flow through the area under treatment. This particular current flow will be maintained by the controlled variable conductance network to accommodate any changes to the conductance presented between the active and return probe by the area under treatment thus ensuring that the electrical current flowing between active and return probes is maintained at the value represented by the output voltage of the DAC. Further, as the voltage output of the DAC varies, the electrical current flowing will vary accordingly. In a particularly preferred embodiment, the output voltage of the DAC is controlled by a digital output of a microprocessor, which may be programmed to provide a varying DAC output voltage, thus causing a similarly varying electrical current flow through an area under treatment. Microprocessor control of the current flow through a treatment subject enables the establishment of treatments that include complex electrical current waveforms that will flow between active and return probes.

The speed of the control loop of the controlled variable conductance network is only limited by the speed of the devices forming the network producing the error, or difference, signal that is input to the base of the transistor, thus controlling the conductance of the variable conductance network.

In another aspect, the present invention provides a method of providing electro stimulation to a subject including the steps of:
(a) attaching a plurality of electro stimulation probes in electrical connection with the subject;
(b) selecting one or more of the probes for connection to at least one electrical power supply thereby causing said one or more probes to become active probes;
(c) selecting one or more of the probes for connection to an electrical current return path thereby causing said one or more probes to become return probes;
(d) connecting said one or more active probes to the at least one electrical power supply and said one or more return probes to the electrical current return path thus causing an electrical current to flow between said active and return probes;
(e) altering the selection of active and return probes; and
(f) repeating steps (d) and (e) until completion.

Preferably, in the instance of providing electro stimulation treatments for a subject, the selection of active and return probes is varied throughout the treatment and in one preferred embodiment, only a single probe is active at any one time whilst only a single probes is also selected as return probe.

In a particularly preferred embodiment, the selection and connection of active and return probes in method steps (d) and (e) are chosen such that during any period of substantially zero current flow in one area of treatment, current flow is established in another area of treatment. These preferred method steps significantly increase the efficiency of treatment by effectively treating two separate areas simultaneously or a single area more intensively.

In yet another aspect, the present invention provides a method of controlling the supply of an electrical current to a subject connected to an electrical power supply unit that is in electrical connection with an area of the subject by at least one active probe and return probe respectively including a first electrical resistance connected in parallel with the at least one active and return probe and having a controllable variable conductance network connected between the junction of the return probe and the first resistance and a ground reference, the method including the following steps:

Initially controlling the variable conductance network to present a low conductance such that limited current can flow through the area of the subject; and subsequently controlling the variable conductance of the network to cause a desired electrical current flow through the area of the subject.

The flexibility to choose the particular probes in a probe set that will supply the electrical signals and those that will form return current paths provides significant advantages with respect to increasing the confidence that an area receives relatively uniform coverage with electrical currents.

Further, in the instance of providing treatments to a subject, choosing probe sets in different areas under treatment to alternately cause electrical currents to flow enables the provision of treatment in one area whilst the other area is subject to an "off cycle". In this instance, the switching of active probe sets allows a significant improvement with respect to the time efficiency of treatments effectively enabling two or more areas to be treated simultaneously thus further reducing the time requirements of subjects requiring treatments. This is a particularly advantageous aspect of the present invention as it simultaneously reduces the time required to effect more than one treatment whilst not requiring the inclusion of an additional power supply which would have the effect of significantly increasing the capital cost of the apparatus.

Whilst the ability to switch probes reduces the accuracy required for placement of the probes on the area requiring treatment, as compared with prior systems and methods, it still remains necessary to obtain a reasonable level of accuracy with respect to probe placement. Accordingly, in a particularly preferred embodiment, a predetermined probe arrangement for a particular part of the body incorporated in a piece of material that may be placed over the area requiring treatment such that the probes are placed in connection with the treatment subject at approximately the required locations. The material may be elasticized and formed in the shape of the area requiring treatment for ease of location on the subject. For example, a pre-determined probe arrangement for a foot may be incorporated into an elasticized piece of material in the shape of a sock, thus enabling the subject to easily place the sock on the foot and hence locate all the probes reasonably accurately for a treatment of the subject's foot.

Of course, in the instance of the subject being a subject, pre-determined probe arrangements for all parts of a subject's body may be established and in the instance of facial treatments, a mask incorporating an arrangement of probes may be placed on the face of a subject thus locating all the probes quickly and easily prior to commencement of an electro stimulation treatment. In the instance of multiple simultaneous treatments to large areas of a subject's body, a body suit of suitable material incorporating pre-determined probe arrangements allows for quick and relatively accurate placement of a large number of probes.

During the provision of electro stimulation signals, a probe should only be either an active probe or a return probe. However, for calibration of the apparatus, a probe may be selected as an active probe and a return probe simultaneously.

For the purposes of this specification, the term probe is intended to include any apparatus capable of providing an electrical connection to the subject of a treatment. For example, the connection could be as a result of direct contact with, or penetration into, the treatment subject or indirect contact by means of an electrolytic solution. Further, the electrical connection could be implemented without any contact such as an inductive connection. For the purposes of describing preferred embodiments of the invention, the provision of electro stimulation signals is described with reference to the treatment of a subject. Accordingly, the term "pad" is used which refers to a probe that is attached to the skin tissue to form an electrical connection therewith. Pads are generally secured to subjects for this form of treatment by some form of adhesive or elastic bands.

BRIEF DESCRIPTION OF THE DRAWINGS

A preferred embodiment of the invention will now be described which should not be considered as limiting any of the statements in the previous section. The preferred embodiment will be described with reference to the following Figures in which:

FIGS. 6A to 6D detail four example electrical current signal patterns between various pads of an eight pad configuration;

FIGS. 8A and 8B detail a standard waveform and a split cycle waveform respectively.

DETAILED DESCRIPTION OF THE INVENTION

Figure 1:
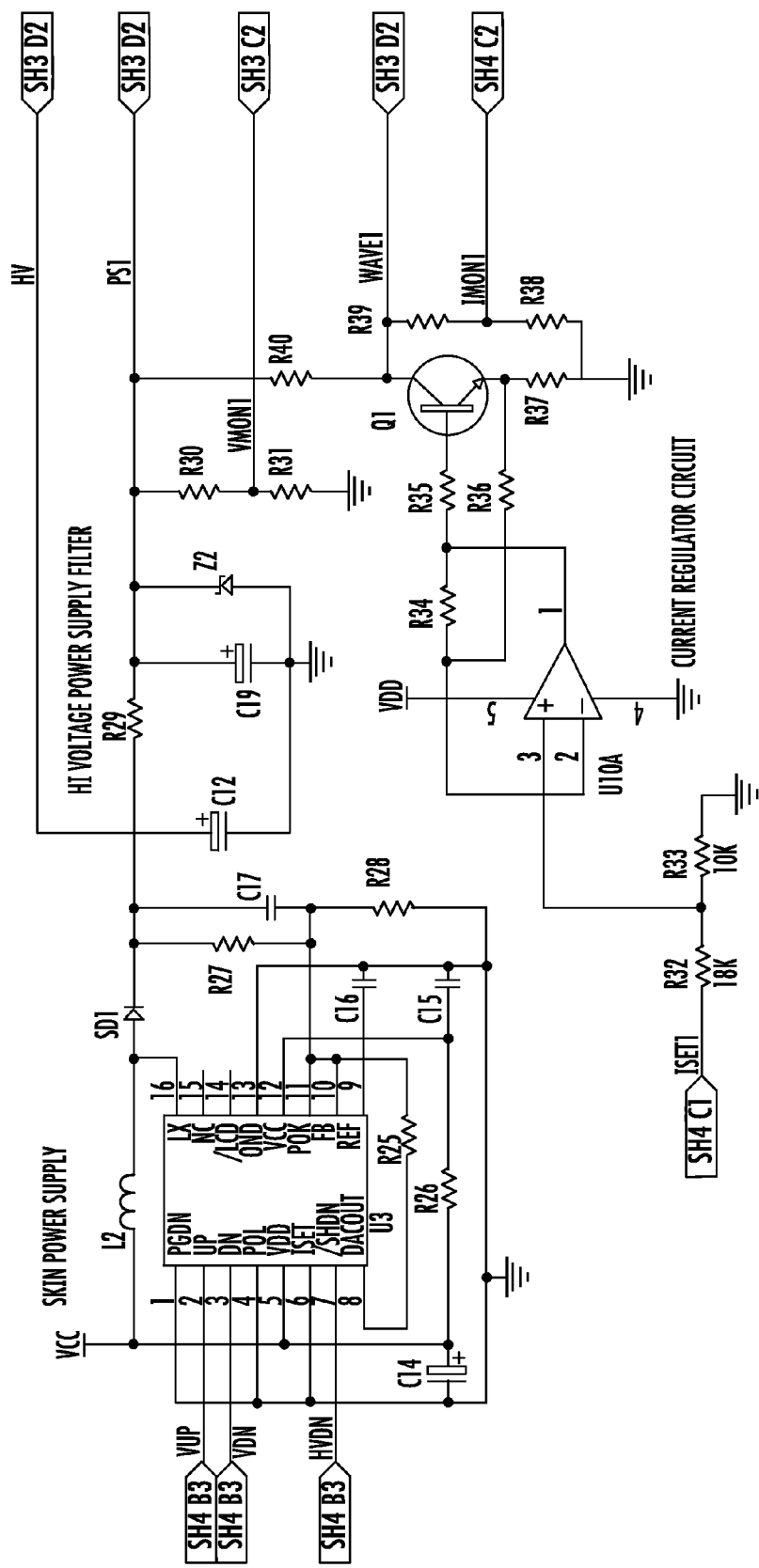
FIG. 1 is a circuit diagram of two separate power supplies and respective current control circuits for the regulation of current supply to the skin tissue of a subject.

With reference to FIG. 1, two power supplies with respective current control circuitry are detailed. In this scheme the output of a power supply is applied to the tissue, however the opposite polarity signal is not derived from the ground or PCB voltage reference signal directly. Instead the current path flows from the positive connection at the power supply through the skin tissue and returns through a controlling transistor, through a sensing resistor to ground. At the junction of the sensing resistor and the transistor emitter is a small voltage that is directly proportional to the current flow through the skin tissue. This voltage is applied to the non-inverting input of an operational amplifier, whose other input is a voltage representing the desired actual current flow. The output of the amplifier controls the voltage at the base of the transistor which directly regulates the current automatically. This circuit is a current regulator.

This scheme leads to superior signal control, and thus more efficient treatment of a subject, and also greatly enhances the ability to effectively switch signals between multiple sources and destinations. In this scheme, high absolute voltages are maintained on the tissue, which promote improved current flow.

In this configuration it is possible to have a multiplicity of current regulator (CR) circuits operating with all circuits supplied by a single power supply. For a single CR there is only one possible current path, from the power supply electrode (PSE) to the CR electrode (CRE), this current will be that set by the voltage on the amplifier inverting input. This voltage is called the Waveform Control Voltage (WCV). If, however there are many CRs each with a CRE, there will be current flow between the PSE and each CRE that is precisely set by the WCV for each CR.

This is one embodiment that represents a simple solution for improving signal distribution (i.e. a single power supply unit with many current regulator circuits). The WCV allows complex current waveforms to be generated in the skin tissue. By varying the WCV signal in a specified and preferred pattern, the current between a CRE and a PSE will match this waveform.

The opposite scenario of a single current regulator and many power supply units is also explored. In this scenario the WCV sets the total current flow for the system. Since electrical current will flow through the path of least resistance, it is difficult to predict the actual signal coverage. This is one embodiment although not a preferred embodiment of the invention.

To advance this to the next logical step it may be seen that if the location of PSE were fixed, the overall signal coverage would comprise a series of lines between the number of CREs used. Although this improves upon existing techniques, it does not provide a significant improvement to the uniformity of signal coverage. It can be observed that if the circuit were able to change the position of the PSE automatically, coverage could be improved. In this simple scenario a high voltage multiplexer integrated circuit (HVMUX) can be used.

Inclusion of a multiplexing device that can receive low voltage signals to effect control of the device enables signals from a low voltage control system such as a microprocessor, to control the distribution of high voltage signals. In one preferred embodiment the HVMUX is an 8:1 configuration. This means that any one of 8 input signals can be selectively switched to one output signal. Alternatively, one input signal can be selectively switched to one of 8 output signals (e.g. any one of eight pads can be selected as an active pad for the supply of an electrical signal to skin tissue). Return pads may be selected in the same way. Of course, there are variations of this arrangement, including 2×4:1, 16:1, etc.

If an HVMUX were used to switch the power supply signal to one of eight possible PSE pads, then a more uniform signal coverage can be obtained. This configuration represents one of the preferred embodiments for a single power supply. (1 PSU, many CR's and many PSE's) The opposite scenario is also possible (many PSU's, 1 CR and many CREs) despite not being a preferred embodiment of the invention.

To further improve the arrangement, it can be seen that by applying a single CR and a single PS to one or more HVMUX circuits that a greatly improved signal coverage can be obtained. However, in this case there is only one signal path at any time.

Other possible scenarios include:
Many PSU's each with 1 CR HVMUX allowing switching of just CR, just PS or both;
1 PSU, many CRs HVMUX allowing switching of CR, PS or both; or
Many PSU's each with 1 or many CR HVMUX allowing all CR, PS, or both to be switched.

Any of the preferred embodiments of the invention that has more than a single CR is capable of generating different current waveforms, by applying different WCV signals to them. The effect of this is to generate more complex waveforms in the tissue than the simple waveforms defined by the WCVs.

Further, since the actual voltage of each PSU may be individually set, the differences between PSU voltages create additional complex signals in the tissue.

Figure 3:
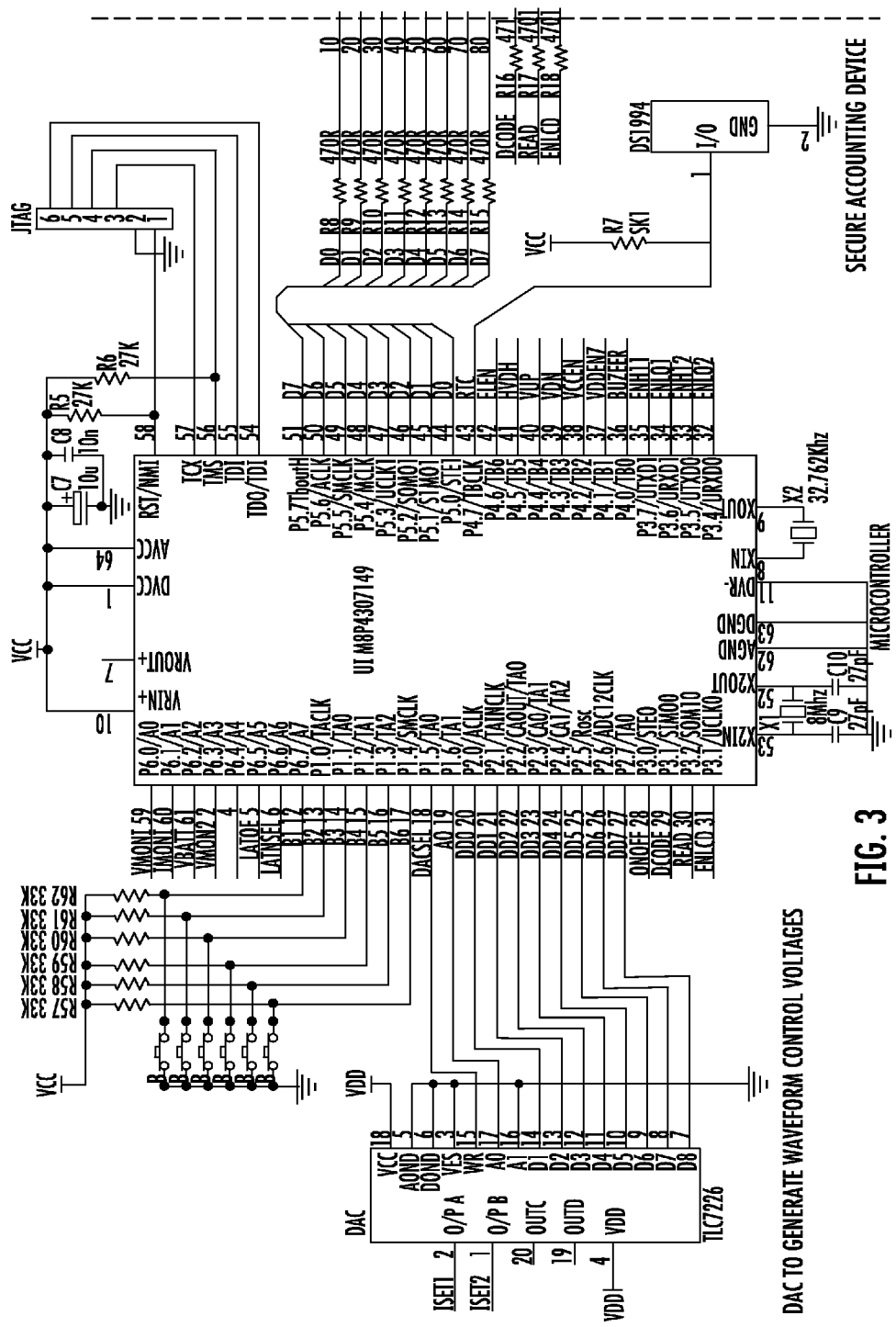
FIG. 3 is a circuit diagram of a microprocessor and a digital to analogue converter.

Each WCV is created wholly independently of the others by a microprocessor circuit (U1, FIG. 3). This microprocessor in a preferred embodiment of the invention also controls the user interface to the apparatus.

Waveforms may be generated or selected for generation from a variety of sources. A preferred set of waveforms may be pre-stored in the microprocessor, or a list of waveform attributes may be selected by the user from a menu or similar collection of predefined values. Similarly, the user may be allowed to define the precise waveform characteristics they require, in which case the microprocessor may calculate the relevant parameters of the waveform in real time.

In a preferred embodiment of the invention, a microprocessor controls one or more independent power supplies and an array of multiplexing/switching devices. The power supply provides an electrical signal and a current return. The switching device is capable of switching a signal or a current return to 1 of 8 pins of the multiplexing device. Thus, in the preferred embodiment, one multiplexing device is used for the switching of the signal and another multiplexing device is used for the switching of current returns to 5 (or more) pins.

Either the signal or a current return can be switched to one of the 8 pins first, then the other may be switched to any of the remaining 7 pins. Thus placing 5 (or more) pads around the area to be treated, a sophisticated switching pattern may be established to stimulate any tissue within the area effectively by activating up to 20 paths for 5 pads (5×4 possibilities), 30 paths for 6 pads (6×5 possibilities), 42 paths for 7 pads (7×6 possibilities) or 56 paths for 8 pads (8×7 possibilities).

Further a plurality of independent power supplies can be switched via multiple sets of multiplexing devices and stimulate more areas or create more intricate and sophisticated stimulation patterns.

Providing a current controlled signal to one pin of the first multiplexing device (U4 FIG. 2) and a return path to one pin of the second multiplexing device (U5 FIG. 2) allows the combination of two padded areas into one and an even more sophisticated stimulation pattern. Similarly more power supplies may be switched similarly allowing a much larger number of current paths.

With reference to FIGS. 1 to 5, a detailed description of the operation of the circuit diagram follows wherein persons skilled in the art will recognize that the circuit arrangement of the invention enables a power supply to generate precise current regulated wave forms for application to the tissue of a subject.

In particular, a control loop is established that substantially reduces "lag" in the control loop as compared with known systems. More particularly, overcoming "lag" in the control loop and effecting control using current regulation, as opposed to voltage regulation, enables numerous advantages to be realized.

With reference to FIG. 1, two separate current regulator circuits are detailed. Although only one of the current regulated circuits will be described, the operation of both of the circuits is identical.

An electrical signal is applied to skin tissue via terminals PS1 and Wave 1, the signals on these terminals being switched through multiplexers U4 and U5 (refer FIG. 2) to probes that are either in direct or indirect contact with the skin tissue of a subject. As a result, the skin tissue of a subject is effectively in parallel with the resistor R40. When the transistor Q1 is in an active mode, there is a flow of current through R40.

When current flows through R40 and the transistor Q1, a voltage appears at the emitter of Q1 which is proportional to the value of the current flow. Effectively, R40, Q1 and R37 form a potential divider between high voltage and ground.

The voltage appearing at the junction of R37 and the emitter is applied to the inverting input of the operational amplifier U10A. The operational amplifiers in the current regulator circuits are configured as differential amplifiers. Accordingly, the signal on the inverting input is compared to the signal present on the non-inverting input which, in the current regulator circuit being described, is a signal called ISET1 scaled by the potential divider formed by resistors R32 and R33. If the voltage at the non-inverting input of the operational amplifier U10A is below the voltage at the inverting input of the operational amplifier U10A, the conductance of the transistor Q1 decreases and, similarly, if the voltage at the non-inverting input is above the voltage at the inverting input, the conductance of the transistor of Q1 is increased. Effectively, Q1 acts as a variable resistor.

As will be recognized by persons skilled in the art, the current regulation circuits detailed in FIG. 1 have a very fast control loop wherein the voltage established as ISET1 causes a current proportional to that voltage to flow through R40. In a preferred embodiment of the invention, the value of R40 is relatively large in order to prevent current spikes when probes are initially attached to the skin of a subject. Electrical current flows though skin tissue in parallel with the current flow through resistor R40 and, if there is a substantial difference in the impedance presented by skin tissue (typically under 30 kohms), the current flowing through resistor R40 can effectively be ignored. For the purpose of considering circuit operation, it is reasonable to consider the current regulator circuits to be measuring the current flow through skin tissue. As the impedance presented to the current regulator circuit, for example, due to changes in the impedance of skin tissue, the current regulator circuit (immediately) adapts to the change in skin tissue impedance to retain the desired current flowing through the tissue.

Accordingly, any voltage signal applied to ISET1 causes a proportional current to flow through the skin tissue. For example, if ISET1 defines a voltage wave form, then a proportional current wave form flows through the skin tissue of the subject.

In the preferred embodiment, the voltage signals ISET1 and ISET2 that cause proportional current flow through the skin tissue of a subject are generated by microprocessor U1 (refer FIG. 3) and by converting a digital representation of a signal value from the microprocessor U1 through the digital to analogue converter (TLC7226).

With further reference to FIG. 3, device DS1994 is a secure accounting device in the form of a secure memory that records the hours of use of the apparatus. In this embodiment, the apparatus is provided to therapists for no basic charge and the therapist only pays for time for which the apparatus is used. In the preferred embodiment, a therapist pays for a number of hours in advance and the secure accounting device tracks the cumulative time for which the apparatus is used and causes deactivation of the apparatus once the operation time for which the apparatus has been paid expires.

Figure 4:
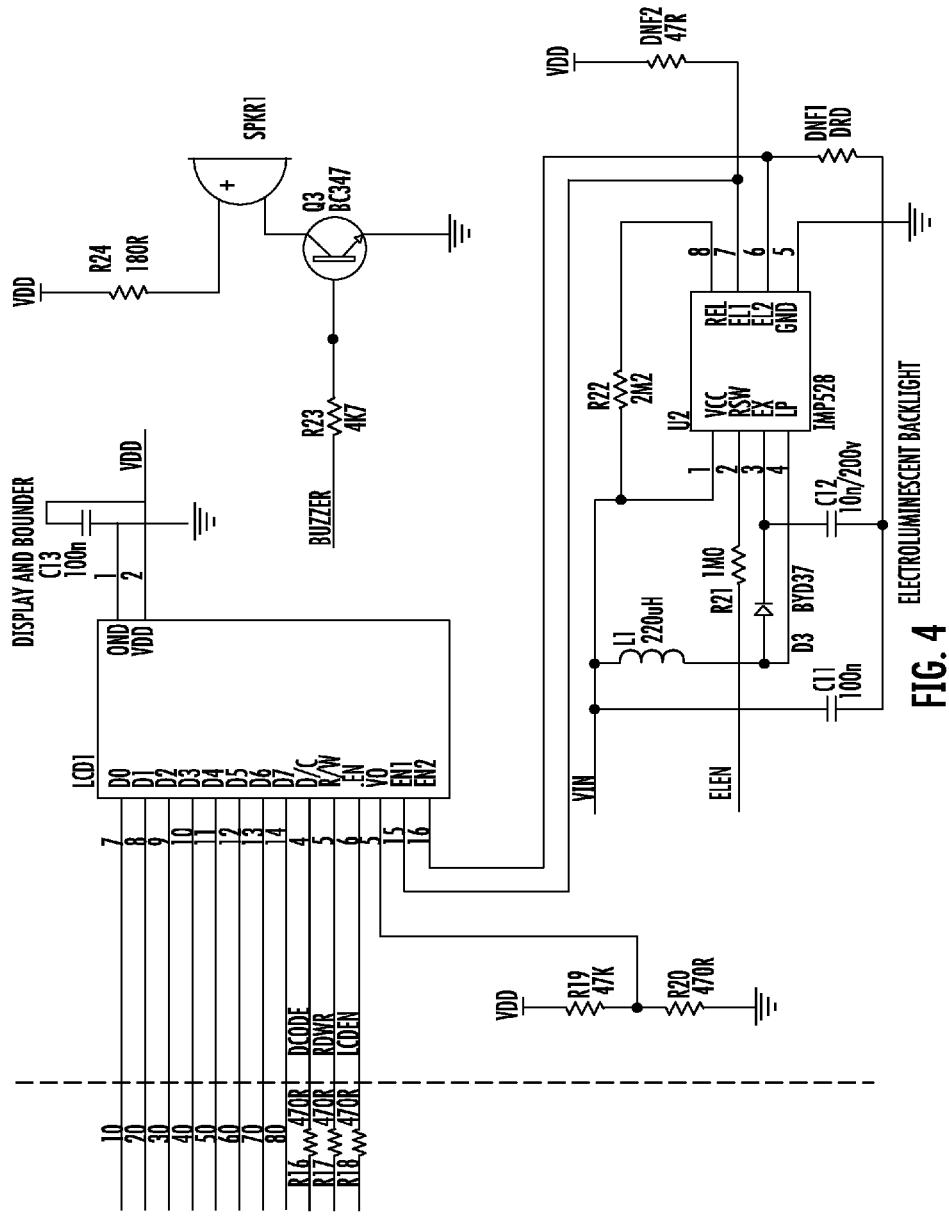
FIG. 4 is a circuit diagram of a display that is connected to the microprocessor of FIG. 3.

With reference to FIG. 4, the device LCD1 is an LCD display that is used to provide information to the operator of the apparatus. Upon activation of the apparatus, the display indicates to the operator the amount of available time remaining to operate the apparatus before the apparatus is automatically deactivated. In addition, the display indicates to operators the treatment that has been selected and the program that has been selected within that particular treatment regime. The display can also indicate the current battery status and any other information relevant to the operational characteristics of the apparatus.

Upon selecting a treatment, the display can also indicate to the operator the amount of time required for that particular treatment and can "count down" the time remaining until cessation of a particular treatment.

In a particularly preferred embodiment of the invention, the display also indicates to the operator the conductivity status of the probes connected to the skin tissue of a subject. In this respect, this information can assist in advising an operator of potential connectivity problems with respect to the skin tissue probes. For example, in the event that skin tissue probes are disconnected from the skin tissue of a subject during a treatment, the information displayed regarding the conductivity between the probes can advise the operator that this condition has occurred enabling them to take corrective action during the treatment process.

With further reference to FIG. 4, the device U2 and associated circuitry forms a power inverter to convert low DC voltages to an AC voltage of 130 volts for the purpose of providing an LCD backlight power supply for the LCD display. Further, Q3, R23 and R24 and speaker SPKR1 provide the apparatus with an audio capability such as sounding a beep in the event that an error condition occurs or to indicate the operation of the user interface.

The user input in the preferred embodiment includes 6 push buttons. The function of these buttons varies depending upon the operating mode of the power supply. Internally, the microprocessor U1 stores several tables of data. These tables include the Treatment Table, the Program Table and the Multiplexer Table.

The Treatment Table currently includes up to 128 different treatments that can be customized through an editor. A Treatment Table currently includes a list of 16 programs, not all of which need be active. Treatments are selected using one of the push buttons (not detailed). This action scrolls through a list of active treatments, displaying the treatment name on the LCD display. The treatment will revert back to the first enabled treatment after the last enabled treatment. Treatments include a list of individual programs which are normally activated sequentially. However to enable treatments to be started part way through a treatment, one of the buttons allows a program within a treatment to be selected and commenced. Currently a treatment may comprise 16 separate programs.

The Program Table includes a list of program parameters. Currently up to 128 programs are may be defined in memory, and may be edited by a built in editor.

Figure 2:
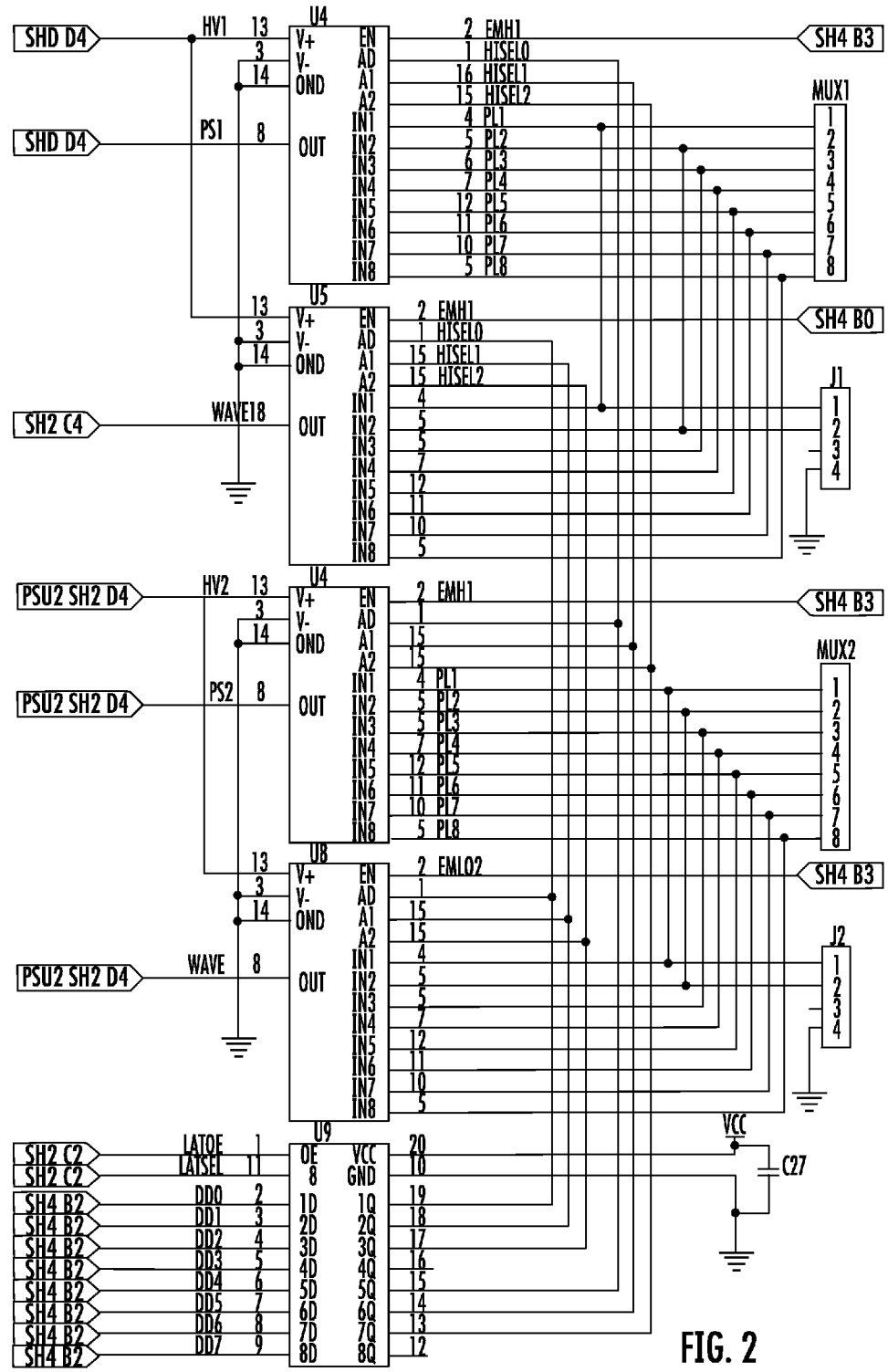
FIG. 2 is a circuit diagram of four separate multiplexing devices.

In addition to generating the signals ISET1 and ISET2, the microprocessor U1 also generates control signals for the multiplexing devices U4, U5, U7 and U8 (refer FIG. 2). Device U9 is a latch that latches eight separate signals from the microprocessor (DD0 to DD7) upon the application of an enable signal to the latch device U9.

Variations of the output signals of the latch device U9 are applied to the selection inputs of the multiplexer devices U4, U5, U7 and U8. The electrical current signal that is to be applied to the skin tissue of a subject appears between the signal lines PSI and Wave 1 and the signal lines PS2 and Wave 2. The regulated electrical current appearing between these respective signal lines is controlled by the respective current regulator circuits detailed in FIG. 1. For the purposes of describing the circuit operation of the preferred embodiment, only operation of multiplexing devices U4 and U5 will be described as the operation of multiplexing devices U7 and U8 is identical.

The supply signal PSI is sourced from the power supply comprising device U3 and associated circuitry (refer FIG. 1). The signal is sourced through resistor R29 which limits electrical current supplied to the skin tissue of a subject and selection of R29 can also ensure that the voltage applied to the skin tissue never exceeds a voltage level that could cause damage to the multiplexing devices.

With reference to device U4 (refer FIG. 2), the input signal ENHI1 effectively controls all the output signals of the multiplexing device and, in the instance that the signal ENHI1 is at a logic low level, there is no power supplied from signal line PSI through device U4. Effectively, the power supply PSI can be completely disconnected from the skin tissue of a subject. The three input signals HISEL0, HISEL1 and HISEL2 enables selection of one of the outputs of the multiplexing device to deliver power supply signal PSI to the skin tissue of a subject. Accordingly, power supply signal PS1 can be applied to any one of the output signal lines of the multiplexing device U4, namely P1_1 to P1_8. Similarly, the multiplexing device U5 may be configured to receive signals from another probe connected to the skin tissue of a subject to form a return current path for electrical current through multiplexing device U5 and provide that return path as signal Wave 1 to the current regulator circuit (refer FIG. 1).

In the preferred embodiment, the multiplexing devices U4 and U5 have their signal lines IN1 to IN8 connected such that upon connection of these individual signal lines to individual pads for application to the skin tissue of a subject, configuration of the multiplexing devices U4 and U5 enables the power supply signal PS1 to be directed to any one of the pads connected to a subject's skin tissue and the establishment of a return current path via any one of the remaining pads. As a result, it is possible to connect eight pads to the skin tissue of a subject and to generate complex current regulated wave forms between the respective pads. The current invention enables the apparatus to be preprogrammed to apply specific signal patterns between one or more respective probes depending upon the region of the body to be treated.

For example, with reference to FIGS. 6A to 6D, a power supply signal may be applied to one pad connected to the skin tissue of a subject with only one other pad acting as a return path for electrical current thus directing the electrical current signal between two specific pads, namely the power supply pad and the return path pad. By selecting different pads to act as the power supply pad and the current return path pad, the current regulated signal passing through the subject's skin tissue may be redirected through those different pads. Applying eight separate pads to the skin tissue of a subject around the region to be treated enables the apparatus of the present invention to apply a range of signal patterns between the pads in order to provide a comprehensive treatment regime to the skin tissue residing between the eight pads.

Figure 7A:
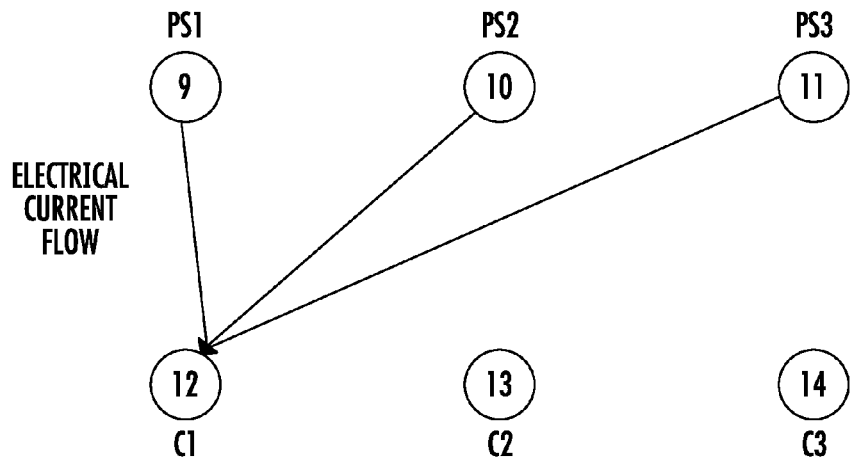
FIGS. 7A and 7B detail example electrical current signal patterns between various pads in an embodiment of the invention that includes a plurality of power signals applied to the skin tissue of a patent.
Figure 7B:
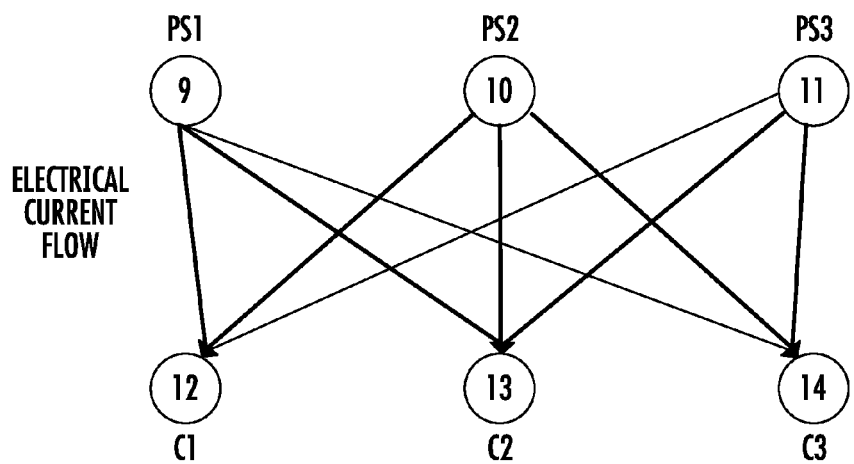

With reference to FIGS. 7A and 7B, the ability of the apparatus of the present invention to provide complex and comprehensive signal coverage to the skin tissue of a subject under treatment is further enhanced when more than one power supply signal is applied to the skin tissue of a subject at one time. For example, with reference to FIG. 7A, three pads providing three respective power supply signals PS1, PS2 and PS3 is depicted with three respective current return path pads C1, C2 and C3. In the particular example of FIG. 7A, three separate power supply signals, PS1, PS2 and PS3, are applied to the skin tissue with only a signal current return path C1 activated. Accordingly, the skin tissue between the pads PS1, PS2 and PS3 and C1 is subject to treatment by the current regulated signals PS1, PS2 and PS3 between the skin tissue to which the pads are connected. Of course, the supply signals PS1, PS2 and PS3 may be supplied sequentially or simultaneously and may even comprise different current wave forms for each of the supply signals.

With reference to FIG. 7B, the complexity of signal distribution through the skin tissue resident between pads PS1, PS2 and PS3 and the return path pads C1, C2 and C3 is significantly increased when electrical current is passed between pads C1 and PS1, C2 and PS1, C3 and PS1, C1 and PS2, C2 and PS2, C3 and PS2, C1 and PS3, C2 and PS3, C3 and PS3.

In the preferred embodiment, each program entry in the Program Table defines the following information which is required to generate a waveform:

1. the waveform frequency;
2. the program duration;
3. the rising slope of the first half of the waveform;
4. the falling slope of the first half of the waveform;
5. the falling slope of the second half of the waveform for split cycle waveforms;
6. the rising slope of the second half of the waveform for split cycle waveforms;
7. the waveform type (including simple, split cycle or compressed cycle);
8. the frequency of polarity changeover;
9. the maximum current flow;
10. the voltage;
11. the number of current regulators; and
12. the Multiplexer Table used for each current regulator.

In this embodiment, there is currently space for up to 128 Multiplexer Tables. Each table includes 64 single byte entries that define the selection status of the pair of multiplexer chips associated with a single current regulator circuit. By creating programs that activate and de-activate different sets of multiplexers for different areas of treatment enables the establishment of many multiplexer sets into a single active set, or more significantly to distribute several multiplexer sets into any required number of active associated sets. Using split cycle waveforms allows the power supply current regulators to be fully utilized in two separate areas requiring treatment by switching the active set of probes from one area to the other during the "off" portion of the cycle in any particular area under treatment.

With reference to FIG. 8A, a typical waveform is detailed that includes a rising slope of a first half of the waveform 18, a period of time at the maximum designated current 20, a falling slope of the first half of the waveform 22 and a period of substantially zero current flow 24 thus completing a waveform cycle. This waveform is substantially repeated at 26, 28, 30 and 32 thus producing a waveform of the desired frequency by selection of the periods of time corresponding with 18, 20, 22 and 24. A split cycle arrangement is detailed in FIG. 8B wherein two separate areas requiring treatment are supplied with two current waveforms I, and 12. During period 34, area 1 is subject to a first half of a waveform 35 whereas area 2 has a substantially zero current flow. However, during period 36, whilst area 1 has a substantially zero current flow, the power supply is switched to a pair of probes in area 2 such that the area residing between these probes is subject to the waveform 37. This process is reversed for period 38 and again for period 40. Subsequent switching of power back and forth between probe sets treating two separate areas enables each area to receive a waveform as depicted in FIG. 8A substantially simultaneously.

Figure 9A:
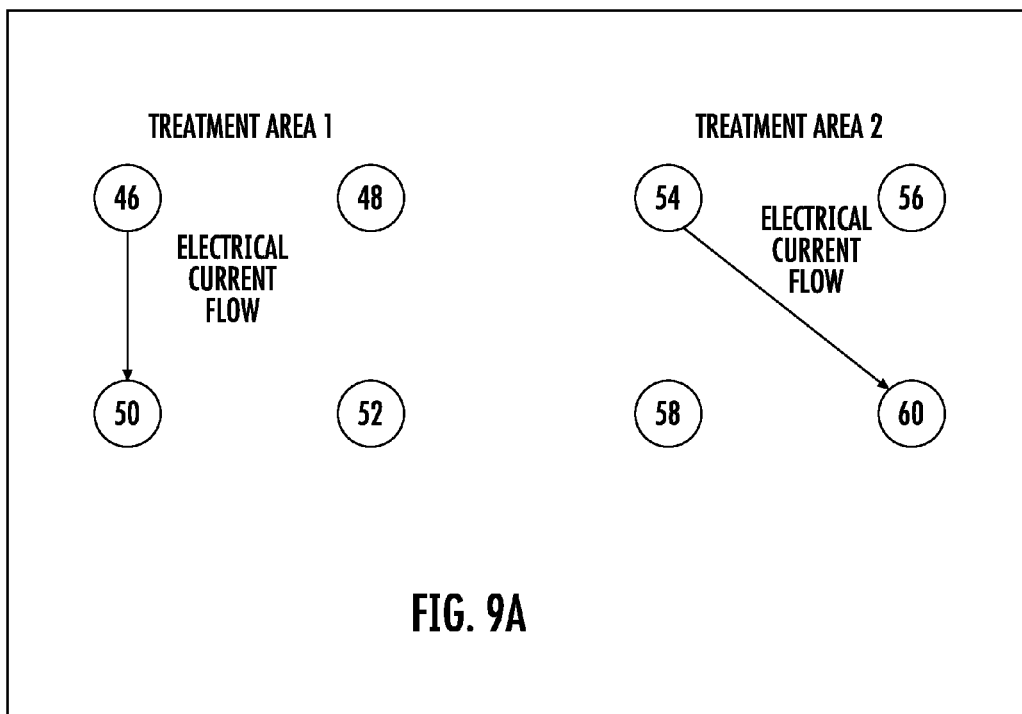
FIG. 9 details an example electrical current signal pattern for two separate areas under treatment using a split cycle approach to effectively treat both areas simultaneously.

With reference to FIG. 9A, an example probe layout is detailed wherein probes 46, 48, 50 and 52 are attached to one treatment area of a subject and probes 54, 56, 58 and 60 are attached to another separate treatment area. During an active half of a cycle, electrical current is caused to flow between probes 46 and 50 in treatment area 1 whilst treatment area 2 is not treated. However, during the "off", or second half, cycle of the waveform for treatment area 1, the power supply is switched to provide a positive first half of a cycle between probes 54 and 60 in treatment area 2. This process continues for the remainder of the treatment with the electrical current being switched between the individual probe sets in treatment areas 1 and 2. Ultimately, upon completion of the treatment programs, both areas will have been treated simultaneously.

Figure 9B:
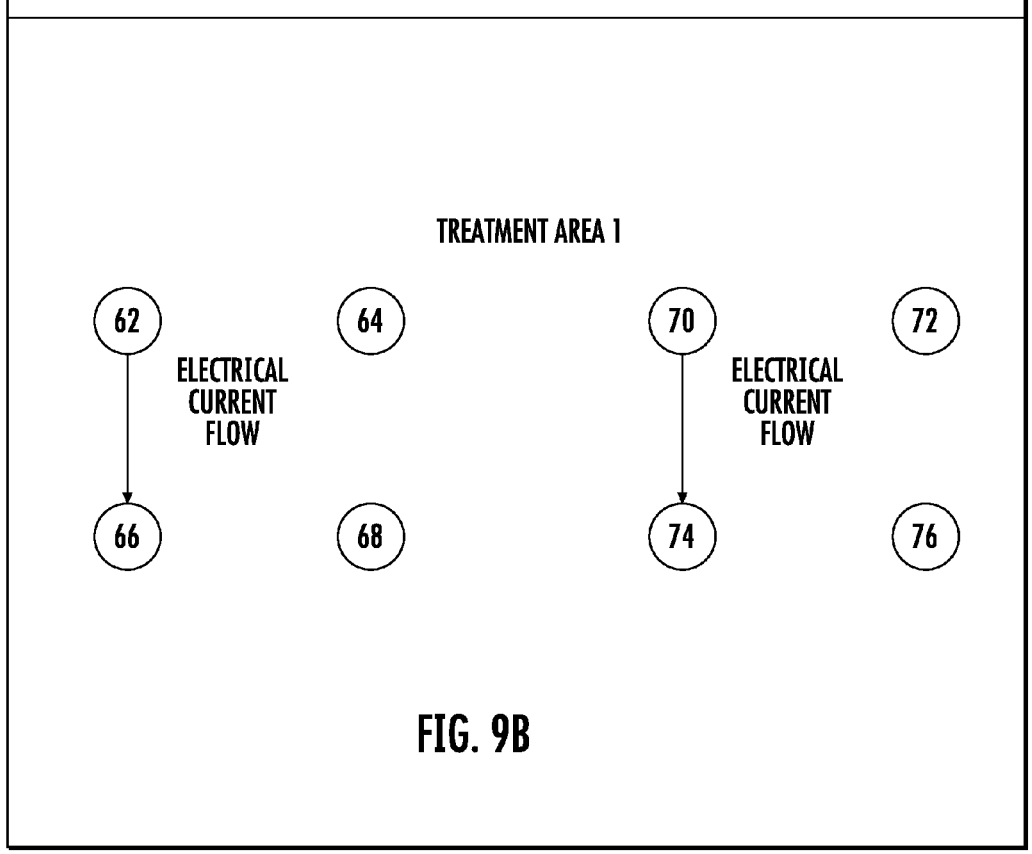

With reference to FIG. 9B, an example probe layout is detailed wherein probes 62, 64, 66 and 68 are attached to one side of a treatment area of a subject and probes 70, 72, 74 and 76 are attached to the other side. During an active half of a cycle, electrical current is caused to flow between probes 62 and 66 on one side of the treatment area whilst the other side is not treated. However, during the "off", or second half, cycle of the waveform the power supply is switched to provide a positive first half of a cycle between probes 70 and 74. This process continues for the remainder of the treatment with the electrical current being switched between the individual probe sets in different sections of the treatment area. Ultimately, upon completion of the treatment programs, the treatment area will have been treated far more intensively or allowed the reduction of the necessary treatment time.

The ability to apply signals to the output of one multiplexer and provide a return current path via another multiplexer and the control of the multiplexer signal lines enables the apparatus to be configured such that the power supply signal supplied from a current regulator circuit bypasses the skin tissue of a subject such that the electrical signal is supplied directly back to the current regulator circuit. In this instance, current flow is through the apparatus itself and this configuration may be used as a test to calibrate the current controlled by the current regulation circuit.

Figure 5:
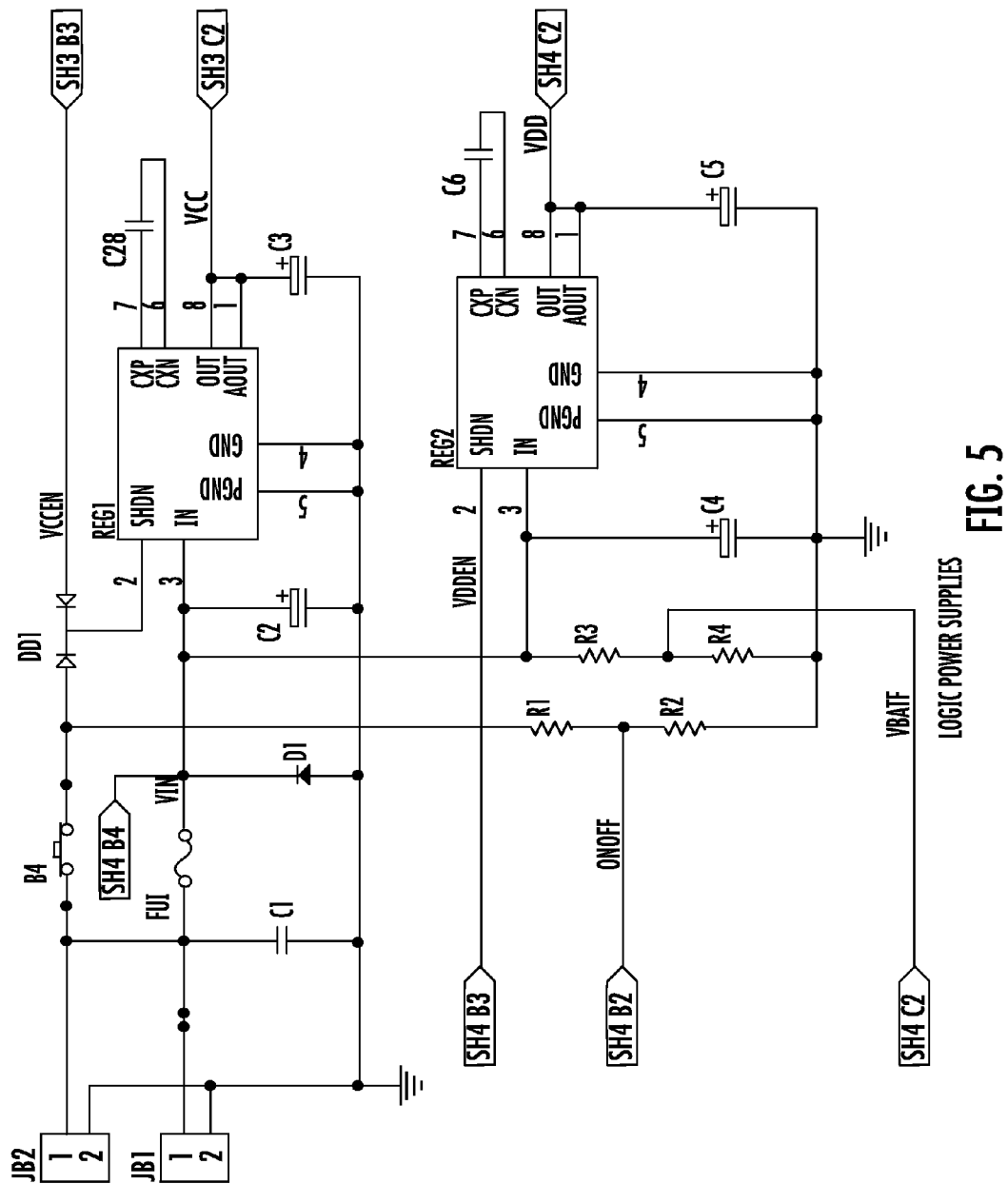
FIG. 5 is a circuit diagram of a conventional power supply arrangement for supplying power to the devices in FIGS. 1 to 4.

With reference to FIG. 5, a circuit diagram is shown detailing a conventional power supply arrangement which is used to supply power to the devices detailed in FIGS. 1 to 4.

CONCLUSION

The improved apparatus and method of the present invention enables the establishment of complex current paths through an area under treatment. Further, application of this type of treatment with an apparatus of the present invention ensures that an area under treatment receives a significantly more uniform treatment as compared with prior systems that rely primarily upon the skill of an operator with respect to the placement of pads.

As a result of improved uniformity of treatment between pads, the placement of the pads becomes less critical and hence it becomes possible for non-skilled users, such as the subjects themselves, to administer treatments. In this respect, a relatively simple set of instructions may be provided guiding the subject with regard to the placement of pads on the skin tissue and the selection of an appropriate treatment program. A significant advantage in this respect is that subjects are no longer required to attend a clinic in order to receive treatments and may apply their own treatment in the comfort of their home at a time that is convenient for the subject. The inclusion of a predetermined arrangement of pads in a piece of material suited to application to a part of the subject's body further assists subjects to apply their own treatments.

In a further improvement to the amount of time required by subjects to have treatments, the ability of the apparatus of the present invention to treat separate areas simultaneously with a single power supply by using the "off" period of a waveform in one area to supply electrical current to another area significantly improves the efficiency of the application of treatments.

The improvements provided by an apparatus according to the present invention are achieved without significantly increasing the number of power supplies contained within the apparatus. As such, an electro stimulation system according to the present invention may be manufactured within an acceptable cost such that the device is considered affordable for purchase and home use by consumers.

An improved apparatus and method according to the present invention further enhances medical aspects of this type of treatment including the healing of wounds, decubitus, fractures, etc. by activating circulation and the tissue activity. It is also possible that an apparatus and method according to the present invention may be used to assist the process of generating or growing tissue and/or cells for skin grafts or other tissue replacement therapies or other purposes. This aspect is particularly beneficial in relation to the treatment of burn victims or any other patients suffering the effect of the removal of skin tissue.

What is claimed is:

1. An electro stimulation system for providing signals to a subject including:
    a first electrical current control circuit (i) adapted for connection to a first electrical power supply such that electrical current supplied to the skin tissue of the subject is controlled and (ii) providing a first electrical current return path;
    a second electrical current control circuit (i) adapted for connection to a second electrical power supply such that electrical current supplied to the skin tissue of the subject is controlled and (ii) providing a second electrical current return path;
    a plurality of first connection probes adapted for temporary external electrical connection to the skin of the subject;
    a plurality of second connection probes adapted for temporary external electrical connection to the skin of the subject;
    a first active switching device for intermittently connecting an output of the first electrical power supply to one of the first connection probes thereby causing the one of the first connection probes to become an active probe;
    a second active switching device for intermittently connecting an output of the second electrical power supply to one of the second connection probes thereby causing the one of the second connection probes to become an active probe;
    a first return switching device configured for intermittently connecting one other of the first connection probes to the first electrical current return path thereby causing the one other of the first connection probes to become a return probe;
    a second return switching device configured for intermittently connecting one other of the second connection probes to the second electrical current return path thereby causing the one other of the second connection probes to become a return probe;
    a first electrical resistance configured to be connected in parallel with active and return probes of the first connection probes;
    a second electrical resistance configured to be connected in parallel with active and return probes of the second connection probes; and
    at least one switching control device connected to the first and second active switching devices and to the first and second return switching devices,
    wherein the at least one switching control device is configured to be activated during a treatment to cause a repeatedly varying selection of different first and second connection probes as active probes or return probes causing a varying formation of electrical currents passing through a path through the skin tissue of the subject with an electrical current being established (i) between an active probe of the first connection probes and a return probe of the first connection probes and a return probe of the second connection probes simultaneously during a treatment and (ii) between an active probe of the second connection probes and the return probe of the second connection probes and the return probe of the first connection probes simultaneously during the treatment.

2. The electro stimulation system according to claim 1 wherein each of the first and second electrical current control circuits is a multiplexing control device and the first and the second return switching devices are multiplexing devices connected to the first and second electrical current control circuits.

3. The electro stimulation system according to claim 2 wherein the multiplexing control devices allows for creation of one or more patterns of repeatedly varying electrical current, wherein the patterns allow for varying stimulation to different layers of the skin based at least in part on electrical current levels and frequency, wherein a treatment comprises one or more patterns of repeatedly varying electrical current.

4. The electro stimulation system according to claim 1, wherein the at least switching control device is configured for reversing the polarity of the active probes such that the active probes become return probes and reversing the polarity of the return probes to become active probes, wherein the reversing allows for uniform stimulation of a specific area of skin tissue of the subject being treated.

5. The electro stimulation system according to claim 1, further comprising a single unit, wherein the first active switching device and the second active switching device are comprised within the single unit.

6. The electro stimulation system according to claim 1, further comprising an arrangement piece, wherein the first and second connection probes are attached to the arrangement piece in a pre-determined spatial relationship relative to each other for connection to the skin tissue of a subject.

7. The electro stimulation system according to claim 1, further comprising a mask, wherein the first and second connection probes are located in spatial relationship to each other by attachment of the probes to the mask, the mask being appropriately dimensioned to align the connection probes in a preferred spatial distribution across a region, or part thereof, of the skin surface of the subject.

8. The electro stimulation system according to claim 7 wherein the mask is a facial mask and the first and second connection probes are located in a spatial relationship to each other that is aligned with the facial region, or part thereof, of a subject.

9. The electro stimulation system according to claim 7 wherein the mask is a body mask and the first and second connection probes are located in a spatial relationship to each other that is aligned with a region of the body, or part thereof, of a subject.

* * * * *